United States Patent [19]

Appelbaum et al.

[11] Patent Number: 5,082,851
[45] Date of Patent: Jan. 21, 1992

[54] PHARMACEUTICAL COMPOSITION FOR PROTECTING THE HEART COMPRISING A HETEROCYCLIC ETHYLENEDIAMINE DERIVATIVE AND METHODS FOR THE USE THEREOF

[75] Inventors: Jerachmiel Y. Appelbaum; Mordechai Chevion; Gideon Uretzky, all of Jerusalem, Israel

[73] Assignees: Hadassah Medical Organization; Yissum Research and Development Corporation of the Hebrew University of Jerusalem, both of Jerusalem, Israel

[21] Appl. No.: 477,046

[22] Filed: Feb. 7, 1990

[30] Foreign Application Priority Data

Feb. 20, 1989 [IL] Israel .......................................... 89349

[51] Int. Cl.$^5$ ............................................ A61K 31/44
[52] U.S. Cl. .................................................... 514/332
[58] Field of Search ........................................ 514/332

[56] References Cited

PUBLICATIONS

Shlafer et al., *J. Thorac. Cardiovasc. Surg.*, 83, 830–839 (1929).
Stewart et al., *J. Thorac. Cardiovasc. Surg.*, 86, 262–272 (1983).
Myers et al., *J. Mol. Cell Cardiol.*, 17, 675–684 (1985).
Meerson et al., *Basic Res. Cardiol.*, 77, 465–485 (1982).
Chem. Abst., III: 111515b (1989). Nagano et al.
Chem. Abst. 103:16658b (1985). Burton.
Chem. Abst. 110:5474 (1989). Aoki et al.

Primary Examiner—Frederick E. Waddell
Assistant Examiner—Zohreh A. Fay
Attorney, Agent, or Firm—Scully, Scott, Murphy & Presser

[57] ABSTRACT

The invention provides a composition for protecting the heart from myocardial ischemia and reperfusion injury as well as for reducing post-ischemic damage, improving cardiac function and serving as a hypothermic cardiac preservative solution comprising N,N,N'N'-tetrakis-(2-pyridylmethyl)-ethylenediamine (TPEN) as active ingredient therein.

6 Claims, No Drawings

PHARMACEUTICAL COMPOSITION FOR PROTECTING THE HEART COMPRISING A HETEROCYCLIC ETHYLENEDIAMINE DERIVATIVE AND METHODS FOR THE USE THEREOF

The present invention relates to a composition for protecting the heart from myocardial ischemic and reperfusion injury.

More particularly the present invention relates to a pharmaceutical composition for reducing post-ischemic damage and improving cardiac function in post-ischemic global and regional myocardial reperfusion following cardiopulmonary bypass, coronary angioplastic thrombolytic procedures and other processes causing myocardial damage in relation to the formation of oxygen free radicals.

The invention also provides a hypothermic organ preservation solution for use in organ transport and transplant procedures.

As reported by D. J. Hearse, (J. Physiol. Paris, 1980, 76, 751-768) during open heart surgery, the practical requirements of the surgeon and the cellular requirements of the myocardium are in direct conflict. The surgeon demands a still, relaxed heart which is unobstructed by catheters and offers a blood-free operating field. By contrast, the myocardial cell ideally requires uninterrupted coronary perfusion with maintained contractile activity. In the last 25 years, attempts to reconcile these conflicting requirements have resulted in the adoption and abandonment of a number of surgical procedures, including potassium citrate arrest coronary perfusion, ventricular fibrillation and ischemic, normothermic and hypothermic arrest. At present, cold chemical cardioplegia is the method of choice in most international centres. This procedure involves aortic cross clamping, with tissue ischemia modified by coronary infusion of cold, chemical solutions and application of topical hypothermia.

It has been found however that reoxygenation following a period of global or regional ischemia may trigger arrhythmias and cardiac damage. Post-ischemic global myocardial reperfusion during cardiopulmonary bypass, coronary angioplastic and other thrombolytic procedures (Goldberg et al. Am. Heart J. 105:26-32, 1983; Balke et al. Am. Heart J. 101:449-456, 1981) are a few of a variety of clinical situations in which arrhythmias and other reperfusion-induced cardiac injuries are experienced.

Recently, the role of oxygen free-radicals in post-ischemic reperfusion associated injury has been studied. Direct evidence for free radical mechanism of reperfusion injury in the heart and the brain have been demonstrated using newly developed methods (Gardner, et al. Surgery 94:423-427, 1983; McCord. J. M. N. Eng. J. Med. 312:159-163, 1985: Shattock et al. Pharmacol. 24:118-122, 1982; Ferrari, et al. J. Mol. Cell Cardiol. 17:937-945, 1985; Gaudeuel Y. and Duvelleroy, M. A. J. Mol. Cell Cardiol. 16:459-470, 1984; Zweier, J. L. J. Biol. Chem. 263:1353-1357, 1988; Zweier, J. L. Circulation Supp III 72:350, 1985: Cao et al. Neurosci. Lett. in press). Furthermore, a possible linkage between such free radicals formation and transition metals release upon ischemia and reoxygenation has been discussed as well (Graf et al J. Biol Chem. 259:3620-3623, 1984 Halliwell, B. FEBS Lett 96:238-242, 1978 Link et al. J Lab Clin. Med. 106:147-153, 1985; Shinar et al. J. Biol. Chem. 258:14778-14783, 1983).

In previous experiments, it has been shown that transition metals, including copper and iron, play an essential mediatory role in reperfusion-induced myocardial damage (Applebaum et al. J. Mol. Cell Cardiol. 19:Suppl. III 150 (Abstr.). 1986: Applebaum et al. J. Mol. Cell Cardiol. 19:Suppl III 150 (Abstr.) 1987). It is assumed that these metals are released from intracellular stores during the ischemic phase, and upon reperfusion, serve as a trigger for the production of oxygen free-radicals via the Fenton and Haber-Weiss Reactions. There are indications that, upon reoxygenation, active oxygen derived species are a major cause of tissue damage in the heart.

In an effort to reduce post-ischemic damage and improve cardiac function after surgical procedures, investigators have experimented with various drugs including Superoxide Dismutase, Catalase, Gluttation Peroxidase, and Allopurinol (Shlafer et al. J. Thorac. Cardiovasc. Surg. 83:830-839, 1982; Stewart et al. J. Thorac. Cardiovasc. Surg. 86:262-272, 1983; Myers et al. J. Mol. Cell Cardiol. 17:675-684, 1985). These drugs focus primarily on scavenging active oxygen free-radicals, however, due to the nature of these short-lived species, only limited protection has been achieved.

A similar problem exists with regard to organ preservation for transport and transplant procedures.

Worldwide, the current concept of myocardial preservation for transplantation includes cold cardioplegic arrest of the donor heart combined with topical cooling followed by storage in ice-cold crystalloid solutions for transplantation. During the transplant procedure, the graft is protected by immersion in cold saline and—most commonly—left sided intracavitary rinsing with cold crystalloids. Clinically, no specific measures to modify reperfusion have been reported as yet.

With this approach, cold ischemic times of 3 to 4 hours have been claimed to be safe, and distant organ procurement is routine in the majority of heart transplant programs. The registry of the International Society of Heart Transplantation, however, has disclosed a strong correlation of early patient survival with cold ischemic times (Fragomeni, L. S. and Kaye, M. P. J. Heart Transpl. 7:249, 1988). The large number of cases available in these statistics reveal a trifold increase in early mortality after transplantation of hearts submitted to 3 to 4 hours of ischemia (15.7%) as compared to those with less than one hour of storage (4.9%). Therefore, myocardial preservation of normal hearts, as required in the setting of clinical transplantation including distant organ procurement still needs to be improved.

The growing need and the development of successful heart transplantation has raised the demand for methods of safe and prolonged storage of donor organs. At present, the conventional storage method allows a safety margin of approximately 4 hours (Thomas et al. Ann. Thorac. Surg. 26:344-350, 1978). The extension of this safe period will enable the increase of the donor pool, will provide adequate time for tissue typing and will allow transportation of donor hearts over long distances.

Several methods of heart preservation have been investigated for this purpose. In experimental studies successful orthopedic transplantation of animal hearts have been reported after 24 hours of Preservation by hypothermic coronary perfusion (Guerraty et al. J. Thorac. Cardiovasc. Surg. 82:531-537, 1981; Wicomb et al. J. Thorac. Cardiovasc. Surg. 83:133-140. 1982; Tago et al. J. Thorac. Cardiovasc. Surg. 86:912-919, 1983; Wicomb et al. Transplantation 34:246-250, 1983; Cooper et al. Cryobiology 20:385-394, 1983; Kioka et al. J. Heart Transplant 5:437-443, 1986; Kaneko et al. J. Heart Transplant 6:8-14, 1987; Takami et al. J. Heart Transplant 7:205-212, 1988) and clinical trials have also been reported (Wicomb et al. Ann. Thorac. Surg. 37:243-248, 1984). Prolonged simple storage in the intracellular-like solution has also been reported with successful transplantation in an experimental study (Reitz et al. Surg. Forum 25:149-151, 1974) These methods of heart preservation have advantages and disadvantages but have not yet been fully investigated, particularly in a comparative study.

Cardioplegic solution by itself is a tool for cardiac preservation during open-heart surgery (Chambers et al. Ann. Thorac. Surg 44:291-297, 1987; Menasche et al. Circulation 76:(suppl. V) V-180-185, 1987). Nevertheless, the large number of past investigations on extended myocardial protection clearly indicates that cold potassium cardioplegia alone has limited capabilities. Accordingly, more recent experimental approaches have focused on the modalities of reperfusion and their implication on post-ischemic myocardial recovery. The important observation of oxygen-induced myocardial damage during reperfusion has led to the concept of applying oxygen free radical scavengers. Oxygen is chiefly reduced directly to water by the cytochrome oxidase system. However, a small proportion is reduced univalently, which results in sequential formation of reactive oxygen intermediates, superoxide radicals ($O_2-$), hydrogen peroxide ($H_2O_2$). and hydroxyl radical ($OH-$) (Chambers et al. Eur. J. Cardiothorax Surg. (in press); Meerson et al. Basic Res. Cardiol. 77:465, 1982). These intermediates can also occur during catecholamine metabolism (Singal et al. Can. J. Physiol. Pharmacol. 60:1390. 1982; Lazar et al. Surg. Forum 60:1353, 1978) urine metabolism involving the xanthine oxidase pathway (Chambers et al. Eur. J. Cardiothorax Surg. (in press): Meerson et al. Basic Res. Cardiol. 77:465, 1982) and the phagocytotic action of phagocytotic action of neutrophils (Lucchesi et al. Do leukocytes influence infarct size limitations Hearse D. J. Yellon D. M., eds. New York, Raven Press 219, 1984; Babior. M. Ca J. Physiol. Pharmacol. 60:1353. 1982: Schopf et al. J. Immunol Meth. 67:109, 1984; Test. S. T. and Weiss, S. J. J. Biol. Chem. 259:399, 1984).

Naturally occurring enzymes are present in aerobic cells for their elimination. Under pathologic conditions, such as ischemia and reperfusion, however, the generation of oxygen free radicals is increased and effective removal by naturally occurring scavenging mechanisms may be impaired.

Several investigations performed in recent years have been based on this biochemical concept. They have studied the effect of exogenous supply of free radical scavengers either to the cardioplegic solution or to the reperfusate. Studies on reperfusion after global myocardial ischemia with SOD or CAT, or both, have included isolated rat hearts (Chambers et al. Eu. J. Cardiothorax Surg. (in press), rabbit and cat hearts (Shlafer et al. J. Thorac Cardiovasc. Surg. 83:830, 1982; Shlafer et al. Circulation 66:185, 1982; Langendorff O. Pflugers. Arch 61:291, 1898), and dogs (Addetia et al. Ann Thorac. Surg. 41:260, 1986; Stewart et al. J. Thorac. Cardiovasc. Surg. 86:262, 1983; Hess et al. J. Cardiofasc. Pharmacol. 5:35, 1983). None of these experiments, however, has focused directly on the situation in cardiac transplantation including global myocardial ischemia at low temperatures for periods of 3 hours or longer.

The essential mediatory role of the transition metals, iron and copper, have already been mentioned. The metals could catalyze free radical induced injurious processes via the "site specific Fenton mechanism". In this mechanism the metal undergoes cyclic single electron redox reactions, yielding the oxygen radicals. These are probably the ultimate damaging species. We have tried to seek protection against ischemia triggered and hydrogen peroxide-induced cardiac damage, by specific chelators, that tightly bind iron and copper and render the corresponding chelates redox inactive.

Prior investigations indicate that the use of metal chelators might inhibit the catalyzing function of transition metals in the formation of the toxic hydroxyl radical.

Thus, rather than attempting to scavenge these short-lived injurious free-radical species, metal chelating agents work to change the redox potential of redox-active metals into an inactive form before free-radical production begins. This protective measure might be a more effective means for reducing post-ischemic cardiac damage.

Previous results following the use of Desferroxamine (Desferal) in the hydrogen-peroxide-induced damaged rat heart demonstrated a limited amount of protection against reperfusion damage. This iron-specific chelators ineffectiveness to eradicate injury is most likely due to its inability to penetrate into the cell. In contrast, Neocuproine, a metal chelator of the o-phenanthroline group, revealed significant protection against both hydrogen-peroxide-induced cardiac damage and reperfusion-induced arrhythmias. However, the results of these experiments clearly indicated that the need for a more protective chelator still existed.

With this state of the art in mind it was an object of the present invention to provide a composition which would serve to protect the heart against reperfusion induced arrhythmias and related cardiac damage in order to achieve full cardiac recovery after hypothermic global ischemia wherein the heart is protected with cardioplegia and which can be used as an excorporeal hypothermic cardiac preservation solution as well as for use as a pharmaceutical composition for e.g. protecting the myocardium during and after open-heart surgery.

Thus according to present invention there is now provided a composition for protecting the heart from myocardial ischemia and reperfusion injury due to metal release and related oxygen radicals formation comprising N,N,N', N'-tetrakis-(2-pyridylmethyl)-ethylenediamine (TPEN) as active ingredient therein in combination with a pharmacologically acceptable carrier.

More specifically the present invention provides a pharmaceutical composition for reducing post-ischemic damage and improving cardiac function comprising N,N,N', N'-tetrakis-(2-pyridylmethyl)-ethylenediamine (TPEN) as active ingredient therein in combination with a pharmacologically acceptable carrier.

The invention also provides a hypothermic cardiac preservative solution comprising TPEN as active ingredient therein and a method for the protection and preservation of excorporeal organs comprising immersing said organ in N,N,N',N'-tetrakis-(2-pyridylmethyl)-ethylenediamine (TPEN) as active ingredient therein in combination with a pharmacologically acceptable carrier.

Preferably the invention provides a composition for protecting the heart from myocardial ischemia and reperfusion comprising a 5 to 7.5 M concentration of TPEN in solution.

TPEN has been known and described in the literature as a complexing agent and metal chelator for over ten years, however, heretofor no one has suggested its surprising efficacy for the compositions of the present invention.

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

Experimental Methodology

The possible intervention of transition metals in the production of oxygen free-radicals was investigated in the ischemic reperfused isolated rat heart model. Simultaneously the protective role of the metal chelator TPEN against reperfusion induced arrhythmias and post-ischemic related cardiac damage was investigated in three experimental models using isolated and retrogradely perfused rat hearts. TPEN (N,N,N'N'-tetrakis (2-pyridylmethyl)-ethylenediamine, a lipid soluble metal chelator with a high affinity for heavy metals and a low affinity for $Ca^{2+}$ and $Mg^{2+}$ was added to the perfusion medium.

EXAMPLE 1

In the first system, the global ischemic model was used and TPEN (7.5 M) was added to the perfusate. After 10 min. of equilibrium, global ischemia was administered for 10 min. followed by 15 min. reperfusion (reopening of perfusate supply). TPEN when added upon reperfusion only showed recovery of 68% in left ventricular pressure (P) and 58% in $+dp/dt$. Nevertheless when TPEN was supplied before ischemia only, recovery of P and $+dp/dt$ improved to 84%, vs. 40% only, in the control group. (See results in Table I).

EXAMPLE 2

The second system examined reperfusion-induced arrhythmias initiated by a temporary ligation of the left anterior descending coronary artery for 10 min. followed by 3 min reperfusion. TPEN, added to the perfusate in concentrations of 5 M to 50 M, showed a dramatic decrease in the incidence and duration of arrhythmias, compared to the control group. The incidence of ventricular fibrillation decreased from a control value of 100% to 0% in the groups with TPEN in concentrations of 10 M, 25 M, and 50 M, and the duration of normal sinus rhythm increased from $17 \pm 1.4$ sec in the control group to the entire 3 minute reperfusion period in these TPEN groups ($p < 0.0000$). These results were coupled by an improvement in post-ischemic recovery of left peak systolic pressure and $\pm dp/dt$. Left ventricular systolic pressure at the end of reperfusion was $26 \pm 18$ mmHg in the control group and improved in the experimental group to $76 \pm 3$ mmHg ($p < 0.01$). (See results in Table II).

In the third experimental model TPEN was used in the cardioplegic solution, which was added to the global ischemic heart every 30 min. during 1 hour of global ischemia in the normothermic experiment and during 3 hours in the hypothermic experiments.

EXAMPLE 3

In normothermic experiments a global ischemia of 60 min at 37° C., after 30 min. of normothermic pre-ischemic perfusion, was introduced and followed by 45 min normothermic reperfusion. TPEN was added to the cardioplegia only in several doses, and 7.5 M TPEN was found to be most efficient with a recovery of 72%, 71% and 69% for P, $+dp/dt$ and $-dp/dt$ respectively in the TPEN treated groups vs. 35%, 35% and 36% for the same parameters in the control group. (See results in Table III).

EXAMPLE 4

In the hypothermic experiments, a global ischemia of 180 min at 10° C., after 30 min of pre-ischemic normothermic perfusion, was introduced and followed by 45 min of normothermic reperfusion. TPEN was mostly effective when supplied both to the cardioplegic solution, and to the Krebs-Henseliet media before and after onset of global ischemia and the hearts revealed pressure recovery of 77% of P VS 61% in the control group. (See results in Table IV).

Upon the experimental results, as described in the Tables, it can be seen that:

1. TPEN completely abolishes reperfusion-induced arrhythmias in the regional ischemic heart model. This phenomenon is coupled with significant improvement in myocardial function which is preserved even when TPEN is administered during the pre-ischemic phase only.

2. TPEN significantly improves the recovery of the global ischemic heart mainly when it is given during the pre-ischemic period.

3. Cardioplegic solution, containing TPEN, protects the normothermic global ischemic heart and improves its post-ischemic recovery.

4. TPEN significantly protects the hypothermic global ischemic heart when added to the cardioplegic solution and administered also in the pre- and post-ischemic period.

5. TPEN is effective in doses as low as 7.5 M, although it reduces ventrical pressure during the pre-ischemic period.

Based on these conclusions the present invention is directed to the use of TPEN in cardioplegic and long-term tissue and cell preservation solutions, as well as in other medical channels and therapeutic methodologies, in order to reduce or eliminate ischemic and reperfusion damage and to prolong tissue and biological cells viability.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A composition for protecting the heart from myocardial ischemia and reperfusion injury comprising a myocardial ischemia and reperfusion injury preventing effective amount of N,N,N', N'-tetrakis-(2-pyridylmethyl)-ethylenediamine and a pharmacologically acceptable carrier.

2. A composition for protecting the heart from myocardial ischemia and reperfusion according to claim 1 comprising a 5 to 7.5 M concentration of N,N,N', N'-tetrakis-(2-pyridylmethyl)-ethylenediamine in solution.

3. A pharmaceutical composition for reducing post-ischemic damage and improving cardiac function comprising a post-ischemic damage reducing effective amount of N,N,N', N'-tetrakis-(2-pyridylmethyl)-ethylenediamine and a pharmacologically acceptable carrier.

4. A method for the protection and preservation of excorporeal organs comprising immersing an excorporeal organ in an excorporeal organ protecting and preserving effective amount of N,N,N', N'-tetrakis-(2-pyridylmethyl)-ethylenediamine.

5. A method for the protection of biological cells from ischemia and oxygen radical related damage comprising immersing biological cells in a solution which includes an ischemia and oxygen radical related damage preventing effective amount of N,N,N', N'-tetrakis-(2-pyridylmethyl)-ethylenediamine.

6. A hypothermic cardiac preservative composition comprising a solution which includes a hypothermic cardiac perserving effective amount of N,N,N', N'-tetrakis-(2-pyridylmethyl)-ethylenediamine and a solvent therefor.

* * * * *